US00PP23360P2

(12) United States Plant Patent
Shipley

(10) Patent No.: US PP23,360 P2
(45) Date of Patent: Jan. 29, 2013

(54) ***PROSOPIS* HYBRID 'LESLIE ROY'**

(50) Latin Name: *Prosopis chilensis×velutina*
Varietal Denomination: Leslie Roy

(76) Inventor: Nicholas Benoit Shipley, Tucson, AZ (US)

( * ) Notice: Subject to any disclaimer, the term of this patent is extended or adjusted under 35 U.S.C. 154(b) by 0 days.

(21) Appl. No.: 13/136,394

(22) Filed: Aug. 1, 2011

(51) Int. Cl.
*A01H 5/00* (2006.01)

(52) U.S. Cl. ..... Plt./216

(58) Field of Classification Search ..... Plt./216, Plt./226
See application file for complete search history.

(56) References Cited

U.S. PATENT DOCUMENTS

| | | | | |
|---|---|---|---|---|
| PP9,072 | P * | 3/1995 | Felker | Plt./216 |
| PP9,256 | P * | 8/1995 | Felker et al. | Plt./216 |
| PP15,303 | P2 * | 11/2004 | Cooper | Plt./226 |

* cited by examiner

*Primary Examiner* — Howard Locker

(57) ABSTRACT

A new and distinct hybrid mesquite tree, *Prosopis* 'Leslie Roy', which is particularly characterized by its thornlessness, its higher tolerance of cold to minus 12c, its semi-evergreen appearance in winter and its upright, outwardly-spreading uniform growth habit. The unique characteristics of this tree result in a landscape tree that is more suitable for parking lots and streetscapes because of its upright habit and thornlessness.

6 Drawing Sheets

Genus: *Prosopis.*
Species: *chilensis×velutina.*
Denomination: 'Leslie Roy'.

BACKGROUND OF THE INVENTION

The present invention relates to a new and distinct cultivar of mesquite tree botanically known as *Prosopis*× and hereinafter referred to by the cultivar name 'Leslie Roy'.

The new mesquite originated from a cross-pollination of an unnamed *Prosopis chilensis* and an unnamed *Prosopis velutina*. The new hybrid mesquite was selected out of 300 trees that resulted from the cross pollination of the two trees by the inventor.

BRIEF SUMMARY OF THE INVENTION

The following traits have been repeatedly observed and are determined to be unique characteristics of 'Leslie Roy'. These characteristics in combination distinguish 'Leslie Roy' as a new and distinct cultivar: 1. Cold tolerance of at least minus 12c. 2. Upright, outwardly spreading growth habit. 3. Thornlessness. 4. Semi-evergreen appearance in winter.

Asexual reproduction of the new cultivar in a controlled environment by softwood cuttings taken in Tucson, Ariz., has shown the unique features of this new hybrid mesquite tree are stable and reproduced true to type in successive generations. The maximum winter hardiness is USDA Zone 7b.

BRIEF DESCRIPTION OF THE DRAWINGS

The accompanying photographs show typical specimens of plant parts of the new variety in color as nearly true as is reasonably possible to accomplish from conventional photographic procedures.

DETAILED BOTANICAL DESCRIPTION

Figure 1:
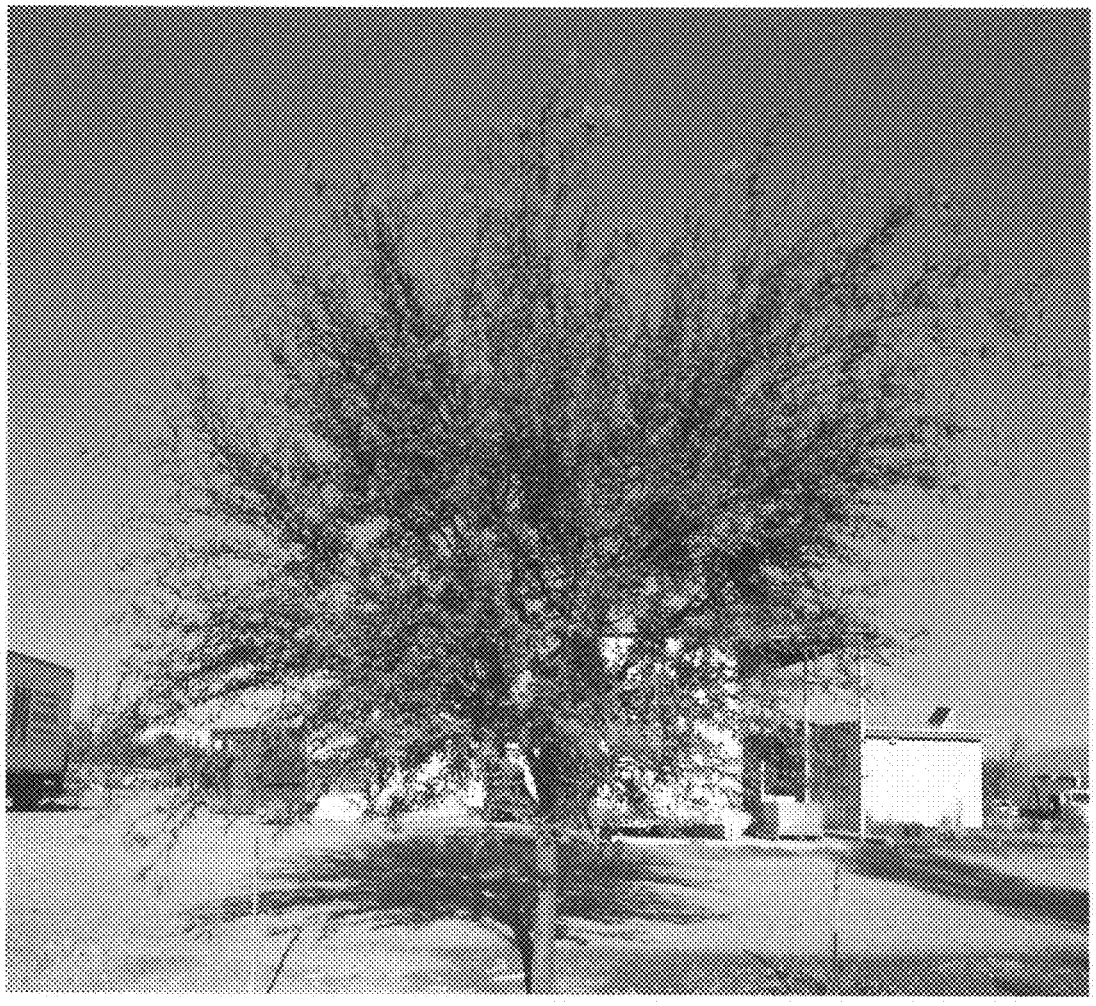
FIG. 1 shows a photograph of the 8 year old original tree of the new variety.
Figure 2:
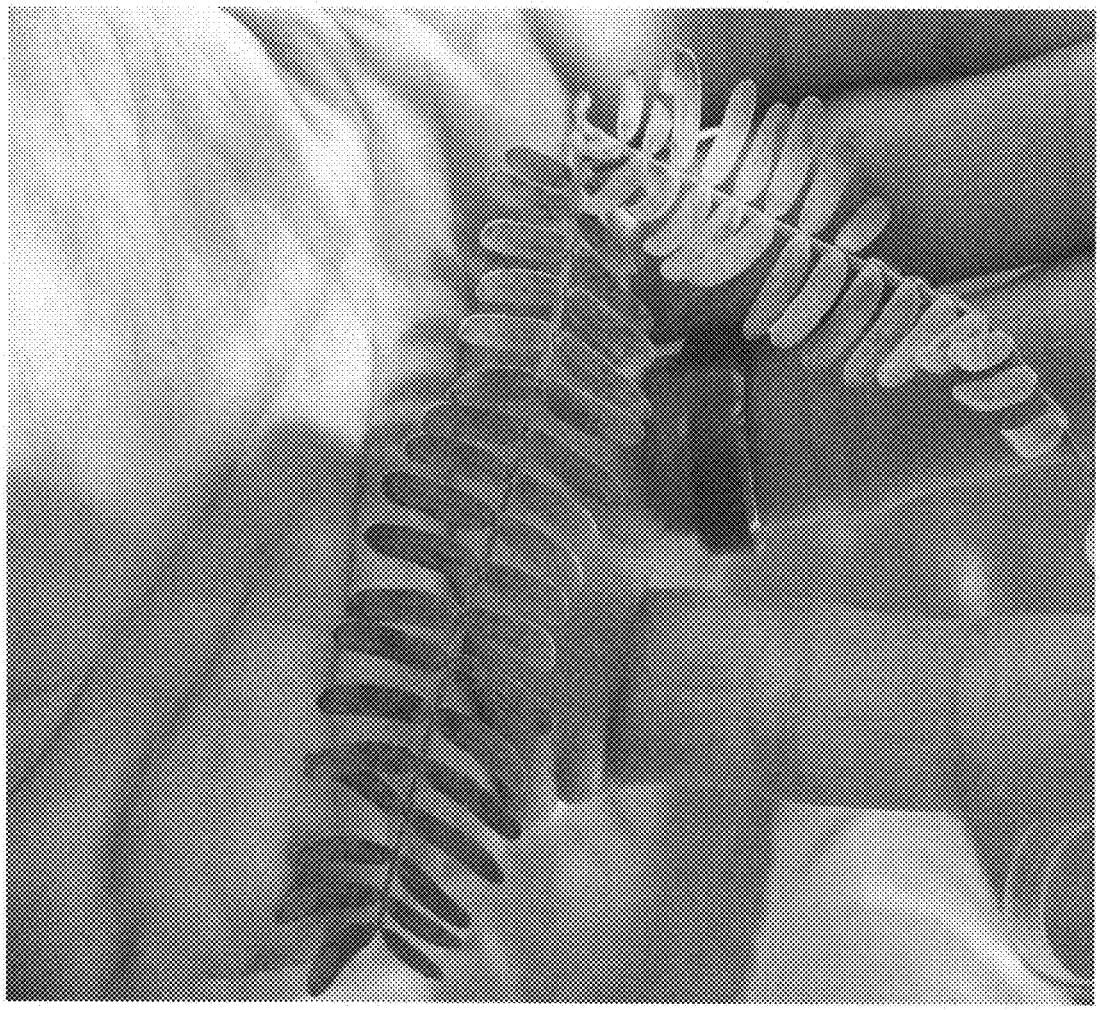
FIG. 2 shows a bipinnately compound leaf in early summer.
Figure 3:
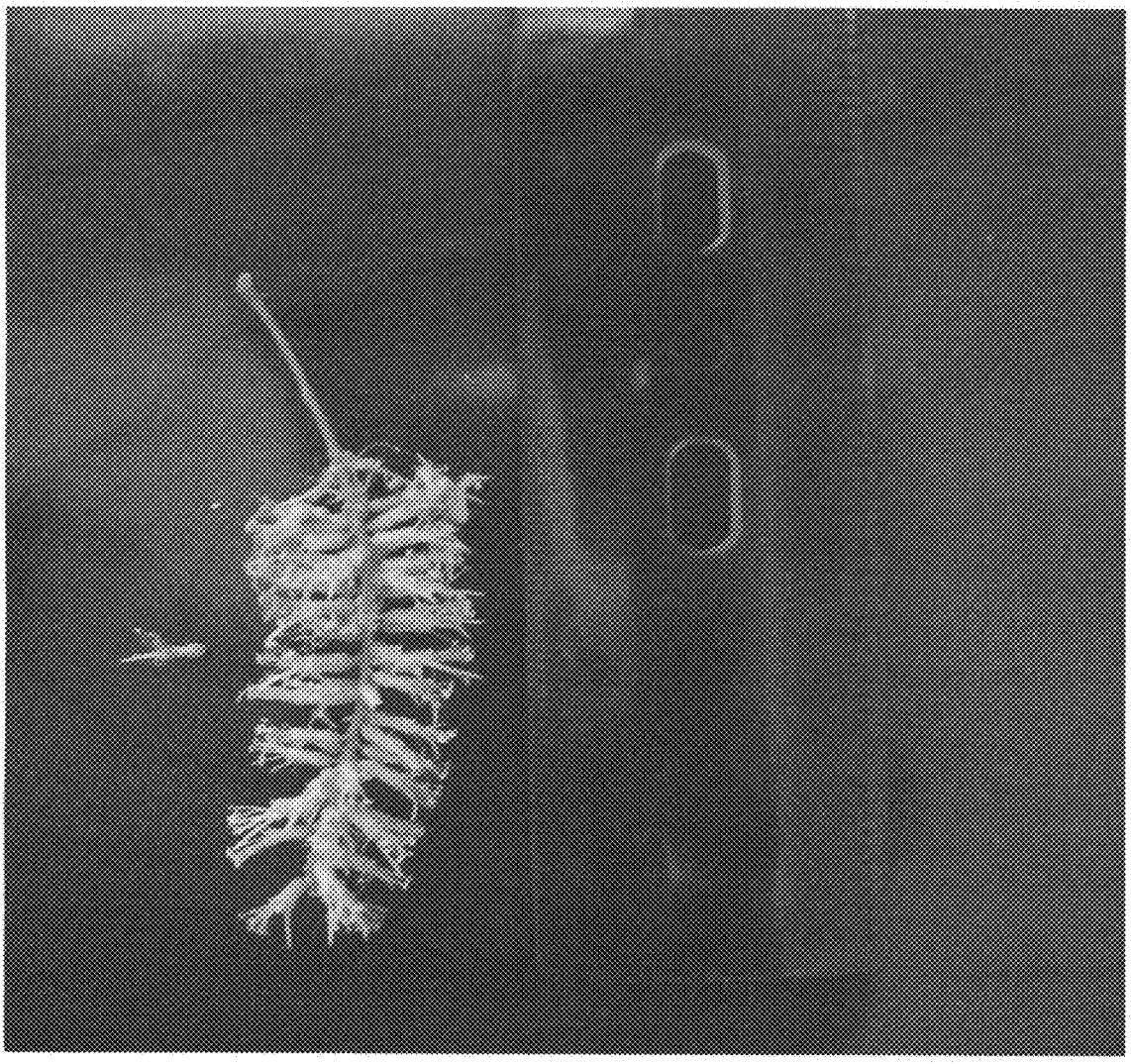
FIG. 3 shows a close up of the flower during the late spring season.
Figure 4:
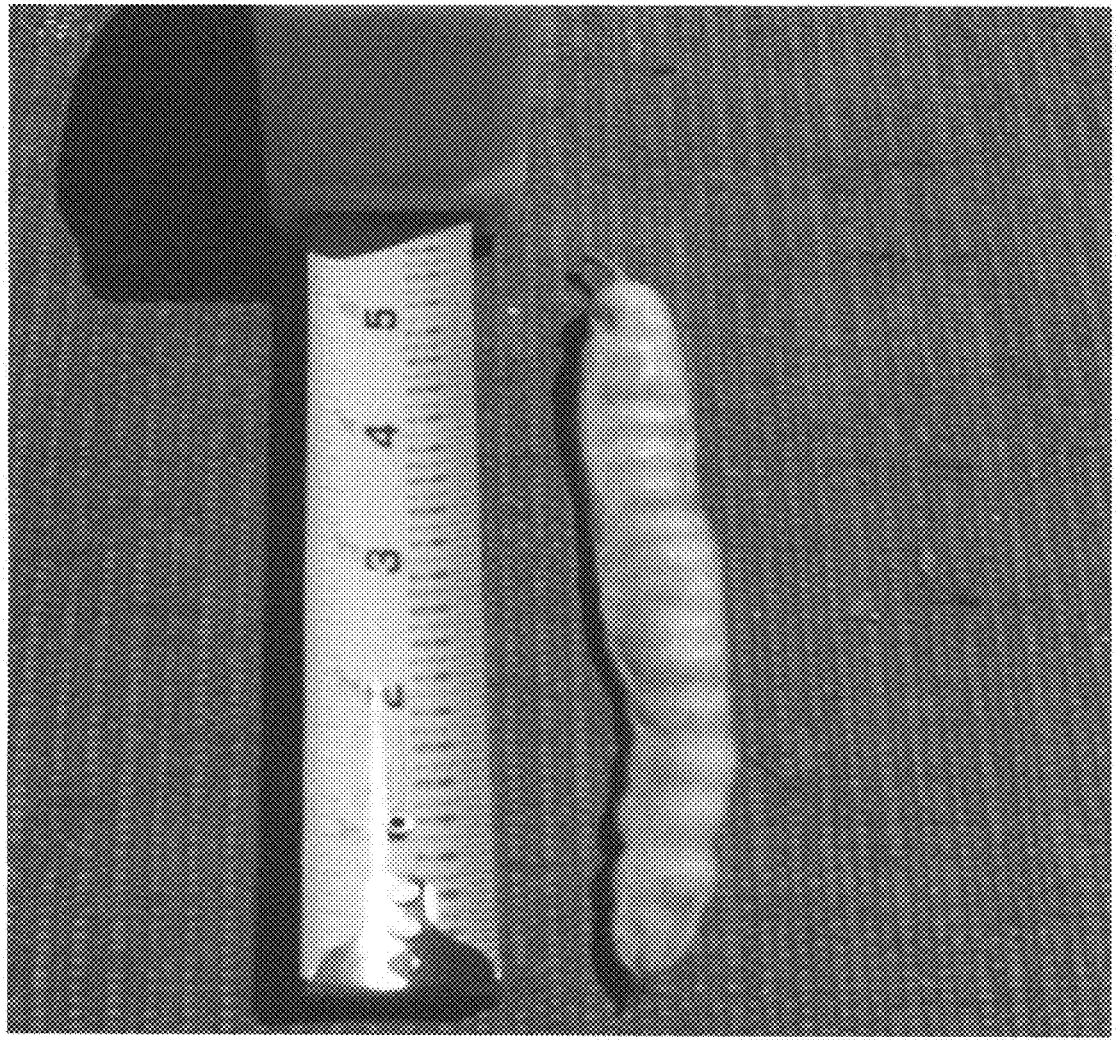
FIG. 4 shows a close up of the fruit.
Figure 5:
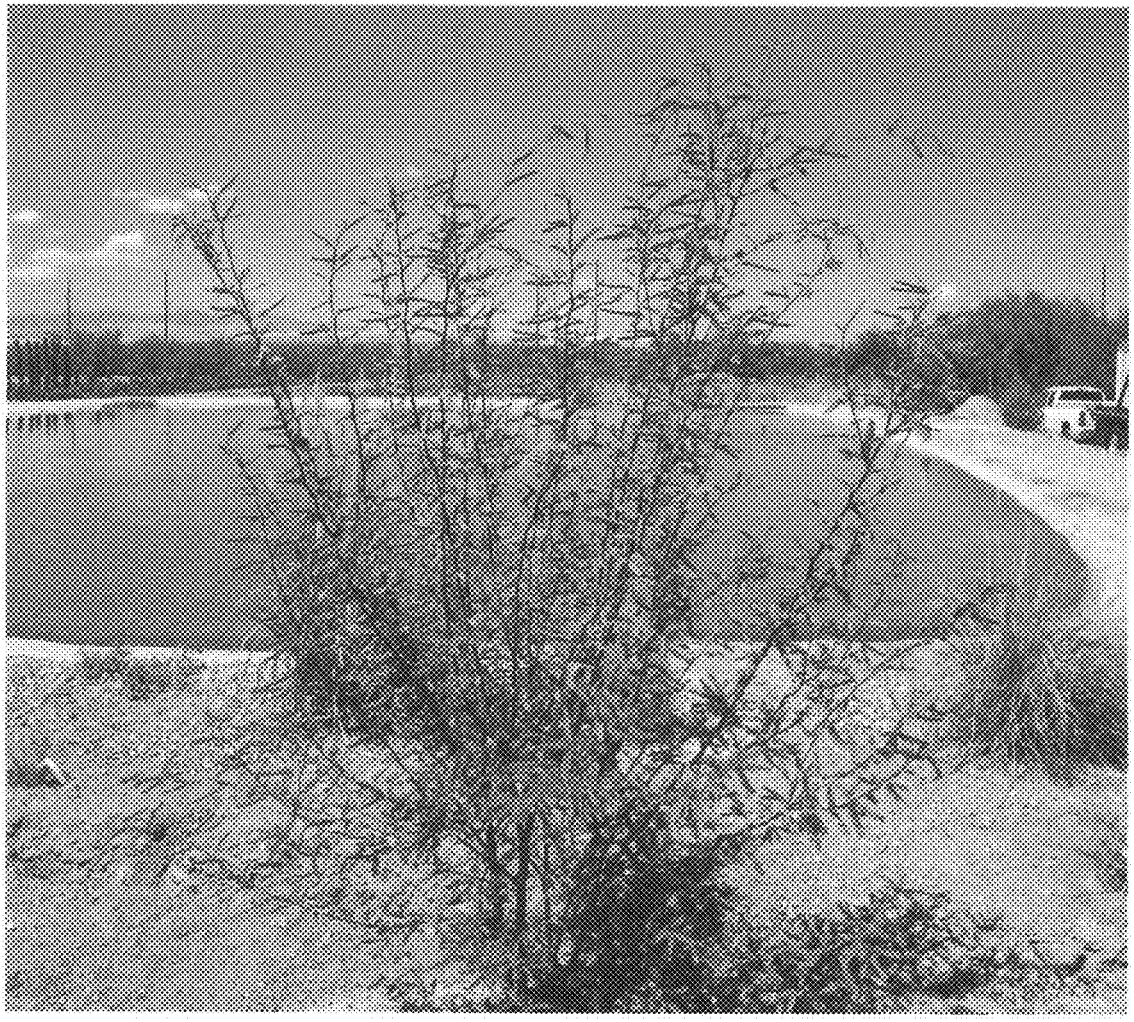
FIG. 5 shows a photograph a juvenile clone of the new variety.
Figure 6:
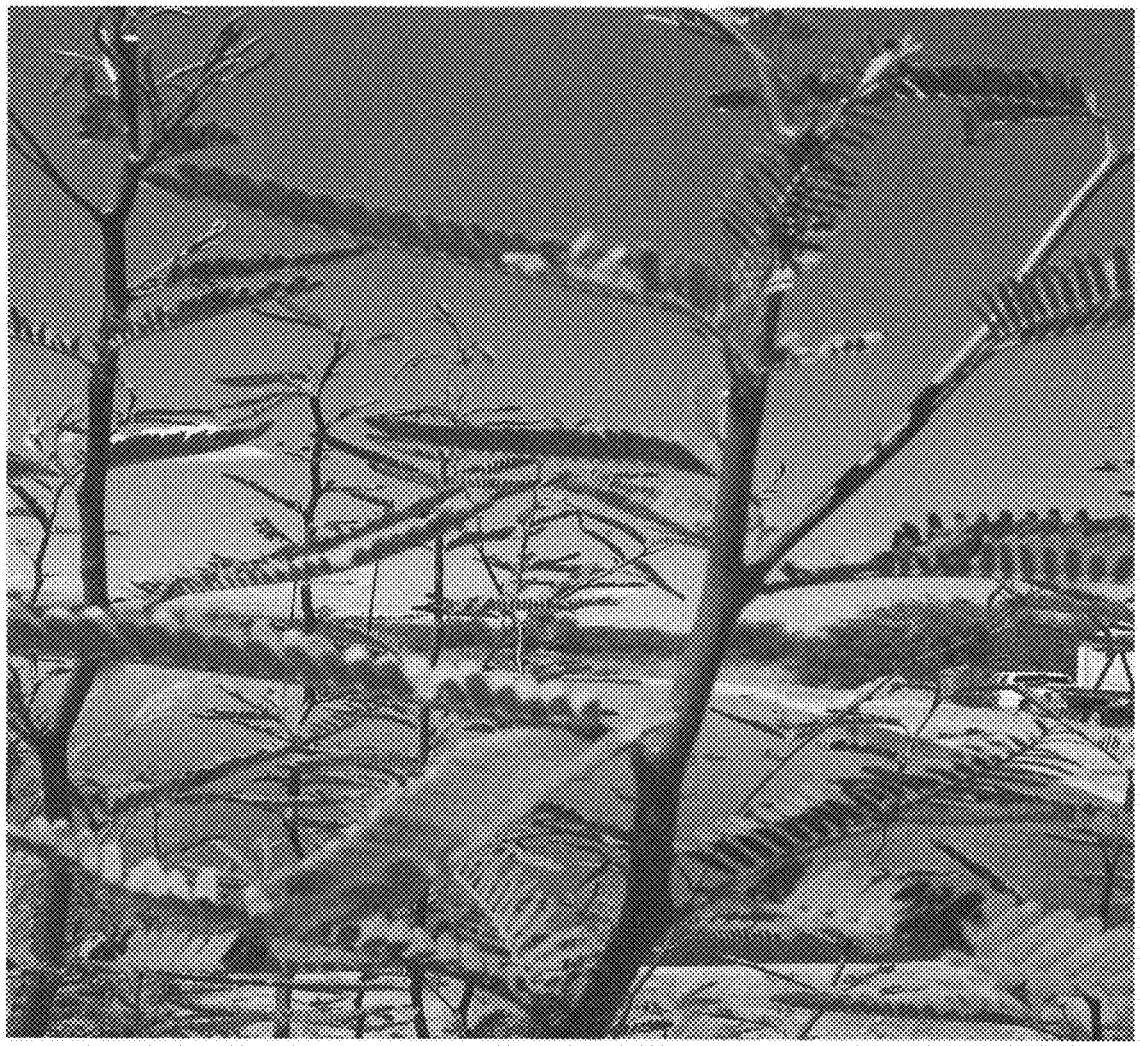
FIG. 6 shows a close up of new growth of the new variety.

The following is a detailed description of *Prosopis* 'Leslie Roy' based on observations made of plants grown and cultured in Tucson, Ariz., according to conventional procedures. The color designations are according to The R.H.S. Colour Chart published in collaboration with The British Colour Council at London, England, except where color terms of dictionary significance are obvious.

Origin: Seedling.

Parentage: A tree propagated from seeds collected from an unnamed plant of *Prosopis chilensis* that was pollinated with an unnamed plant of *Prosopis velutina* in Tucson, Ariz.

Classification: *Prosopis* 'Leslie Roy'.

Form: Moderate size. Upright, outwardly-spreading growth habit.

Height: Mature height approximately 30 ft and 30 ft wide.

Growth: Abundant with a multi trunk and spreading ascending branches, with a crown that has an open form. Fast growing at the rate of 3-4 feet per year.

Branches: Internodes short, 3 to 5 cm long. The first years shoots are smooth and slightly zigzagged in form, 5 mm to 1.5 cm in diameter and are in color group RHS 187A. Branches of 4 cm to 7 cm in diameter are in color group RHS 197B and have a smooth texture.

Bark: The mature bark on the trunk of the original 8 year old tree is rough and scaly and is in color group RHS N200.

Foliage: Alternate, bipinnately compound, 8-9 cm long and 2.5 cm wide. Green group, RHS 137D, slightly de-current on a short 1.5 to 2 cm petiole. Leaves usually found in pairs (occasionally found with 2 or 3 pairs). Each leaf has 18-27 pairs of minor leaflets per leaf with a leaf stock length of 7-9 cm. Leaflets are 1.2 cm long, 3 mm wide, with a spacing of 2 mm. New growth has slight pubescence.

Inflorescence: Raceme, 5 cm long and 1.7 cm wide; 260-280 flowers per inflorescence shoot.

Flowers: Bisexual, radial, yellow orange group RHS 21C. Blooms mid April to end of May, has one flower cycle. Calyx is shallow and bell shaped with short lobes. Corolla, free, 2 mm. Pistil appears before stamens. Stamen 10, free.

Fruit: 14-17 cm long, 1.5 cm wide, 4 mm thick, color group yellow-orange RHS 14D, linear drop from the tree in late June as they ripen.

Seed: 7 mm long and 4 mm wide with a color group grey-orange RHS 165A; 10 seed count weight is 440 mg.

Hardiness: February 2011 'Leslie Roy' withstood 4 consecutive days at minus 8c, with a minimum temperature of minus 12c, no damage occurred. The maximum temperature experienced 45c with no damage. Little water is required for 'Leslie Roy' to thrive in Tucson with an average annual rain fall of 11 inches. 'Leslie Roy' mesquite is semi-evergreen down to minus 6c.

Disease resistance: This hybrid is not known to be susceptible to any soil borne pathogens or to any foliar disease. The plant has not been observed to suffer from any insect infestations.

It is claimed:

1. A new and distinct cultivar of mesquite tree named 'Leslie Roy', as illustrated and described.

* * * * *